United States Patent [19]
Hergeth

[11] Patent Number: 5,692,622
[45] Date of Patent: Dec. 2, 1997

[54] PROCESS FOR THE RECOGNITION AND FILTERING OUT OF DIFFERENTLY COLORED FOREIGN BODIES IN FIBRE PROCESSING LINES

[76] Inventor: Hubert A. Hergeth, Konigsmuhlenweg 11, 52076 Aachen, Germany

[21] Appl. No.: 721,974

[22] Filed: Sep. 27, 1996

Related U.S. Application Data

[63] Continuation of Ser. No. 344,819, Nov. 23, 1994, abandoned.

[30] Foreign Application Priority Data

Nov. 25, 1993 [DE] Germany .................... 43 40 173.2

[51] Int. Cl.⁶ .................................................. B07C 5/342
[52] U.S. Cl. ........................ 209/580; 209/587; 209/639; 209/938; 209/939; 356/402
[58] Field of Search ................................ 209/576, 577, 209/580, 581, 582, 587, 639, 938, 939; 356/402, 407; 250/226; 100/144

[56] References Cited

U.S. PATENT DOCUMENTS

| | | | |
|---|---|---|---|
| 4,657,144 | 4/1987 | Martin et al. | 209/581 X |
| 4,718,558 | 1/1988 | Castaneda | 209/581 X |
| 4,765,489 | 8/1988 | Satake | 209/587 X |
| 5,215,772 | 6/1993 | Roth | 209/577 X |
| 5,383,135 | 1/1995 | Shofner et al. | 364/552 |

FOREIGN PATENT DOCUMENTS

| | | | |
|---|---|---|---|
| 5169037 | 7/1993 | Japan | 209/587 |

*Primary Examiner*—Tuan Nguyen
*Attorney, Agent, or Firm*—Lockwood, Alex, Fitzgibbon & Cummings

[57] ABSTRACT

The invention relates to a process which enables colored foreign bodies to be detected in continuous fibre transport and removed therefrom. A stream of fibres is examined for foreign bodies by color sensors (11). If the color differs, a control system (12) activates compressed air nozzles (13) and removes foreign bodies (17).

6 Claims, 1 Drawing Sheet

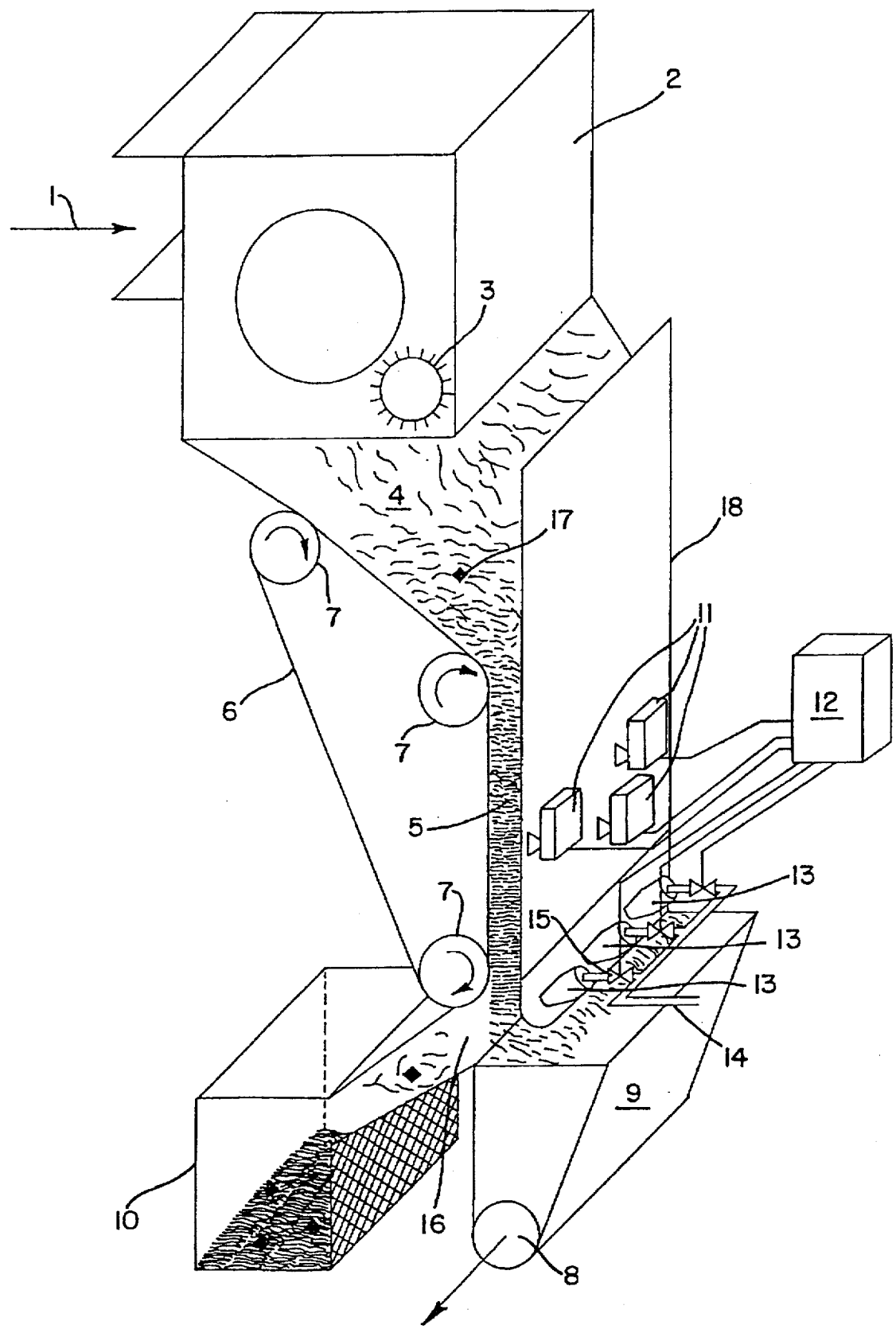

PROCESS FOR THE RECOGNITION AND FILTERING OUT OF DIFFERENTLY COLORED FOREIGN BODIES IN FIBRE PROCESSING LINES

This application is a continuation of application Ser. No. 08/344,819, filed Nov. 23, 1994, now abandoned.

For almost 10 years attempts have been made, more particularly in the cotton processing industry, to recognize foreign bodies in the cotton by optoelectronic methods. Such foreign bodies such as, for example, plastics foils, nylon cords or coloured headscarves, lead to spinning machinery malfunctions or give rise to expensive claims. Proposals have been made to install electronic cameras on the cutting heads of fibre bales, the surface of the bales being inspected during cutting down. The electronic camera is equipped with an evaluating computer which analyzes the signals and, when limit values are exceeded, triggers an alarm or briefly diverts the flow of production. The difficulties of such a system are represented by the excessive quantity of data to be processed, the poor color differentiating possibilities of the camera and the optical imprecisions due to the uneven surface and vibrations. Up to date no satisfactorily operating installation of this kind has become known.

The only known system of which a few examples are operating in practice is a Japanese construction. In that construction the fibres are blown into a shaft, the column of fibrous material thus formed stays still for an instant, and an electronic camera observes the fibres through a transparent sheet. An elaborate electronic evaluating system evaluates the signals delivered by the camera. Since the area to be examined is approximately 1 m$^2$, an appreciable time (approximately 1 second) elapses until the computer has recognized that the material is satisfactory or contains colored elements. In dependence on the result of evaluation, the fibres are conducted via a switch to the processing operation or they are removed. Then the shaft is refilled with fibres. Due to the long evaluation time, the result is intermittent operation and the throughput is too small for the usual production lines. In the case of similar colors, such as white/yellow, the color differentiation is still inadequate.

It is an object of the invention to provide a simple inexpensive system for the separation of colored foreign bodies which has a high throughput and does not separate many satisfactory fibres. According to the invention this is achieved by the use of a plurality of color sensors which inspect a column of material as it passes through and purposefully separate the foreign components from the body of fibres.

The invention will now be described with reference to the drawing. The fibres are removed by suction from a bale cutter through a condenser (2), moving via a connecting member (1) into the condenser (2); then, after passing a filtering-out drum (3), they are delivered unpressurized to a chute (4). The fibres are compacted in a shaft (5) formed by a transparent sheet (18) and a conveyor belt (6), which runs around rollers (7). Starting in the chute the conveyor belt compacts the fibres, which it conveys along the glass sheet (18).

Disposed at a number of levels on the outside of the sheet (18) are color sensors (11), for example, Yamatake CS70-CA1. The sensors are distributed in a direction substantially 90° to the conveying direction of the fibres and observe only a small portion of the fibre mat, for example, 1 cm$^2$ thereof. However, the color sensors are so disposed so that foreign bodies smaller than 1 cm$^2$ of projected surface are not inspected by two color sensors during transport. This portion is illuminated with a constant light from the sensor unit, and the reflected light is evaluated in accordance with its components of the 3 basic colors (red, green, blue) and also its intensity and saturation.

The differentiation between "satisfactory" and color deviation can be performed on the basis of values provided from outside by the control unit (12) or via a "teach-in". In a "teach-in", fibrous material is conducted under supervision through the shaft, and the average color determined is stored as the "satisfactory" color. The color sensors are distributed over the width of the shaft and offset at different heights, so that they do not affect one another.

If the sensors do not detect any foreign component (17), the fibre mat drops into a suctional removal chute (9) and is removed by suction via a negative pressure line (8). If one of the sensors (11) detects a color deviation, an output is actuated so that the event is announced to the control system (12). The control system actuates with delay, in accordance with the speed of the belt (6), the valve (15) of the corresponding air nozzles (13), so that the foreign body (17) and only very few fibres are blown by the air flow produced into a channel (16). The valves are supplied with compressed air via a common pneumatic line (14). The filtered-out bodies are collected in a box (10).

The use of individual sensors enables the mass of fibres to be analyzed and evaluated very rapidly. Intermittent operation is unnecessary. The offset arrangement of the color sensors enables the fibres in the shaft to be continuously monitored. The selected removal allows the color sensors to be very sensitively adjusted, without the removal of too many satisfactory fibres.

I claim:

1. A process for the recognition and filtering out of differently colored foreign bodies from fibre flocks in processing lines, said process including the steps of:

continuously transporting the fibres over a measuring distance and past a plurality of color sensors to detect the presence of said foreign bodies in the fibre flocks; and compacting the fibres in a converging shaft, one wall of which is formed by a conveyor belt which moves the fibres along and past the color sensors;

the color sensors being distributed in a direction substantially 90° to the transporting direction.

2. The process according to claim 1, wherein the color sensors are so disposed that foreign bodies smaller than 1 cm$^2$ of projected surface are not inspected by two color sensors during transport.

3. The process according to claim 1, wherein each of the individual color sensors has its own illumination source incorporated therein for the inspection.

4. The process according to claim 1, including a control system which actuates ejectors corresponding to the sensors, and the actuation of the ejectors is delayed in response to the transport speed of the fibres.

5. The process according to claim 1, including one to five color sensors each of which has a solenoid associated therewith which actuates a compressed air ejector nozzle in accordance with the signal of its associated color sensor.

6. A process for the recognition and filtering out of differently colored foreign bodies from the fibre flocks in processing lines, said process including the steps of:

continuously transporting the fibres over a measuring distance and past a plurality of color sensors to detect the presence of the foreign bodies in the fibre flocks; and compacting the fibres in a converging shaft, one wall of which is formed by a conveyor belt which moves the fibres along and past the color sensors;

wherein one to five color sensors are provided each of which has a solenoid associated therewith which actuates a compressed air ejector nozzle in accordance with the signal of its associated color sensor.

* * * * *